(12) United States Patent
Depenheuer et al.

(10) Patent No.: US 9,453,765 B2
(45) Date of Patent: Sep. 27, 2016

(54) METHOD FOR MEASURING CONCENTRATION OF A GAS COMPONENT IN A MEASUREMENT GAS

(71) Applicants: Daniel Depenheuer, Jockgrim (DE); Thomas Hankiewicz, Karlsruhe (DE); Frank Probst, Herxheim bei Landau/Pfalz (DE)

(72) Inventors: Daniel Depenheuer, Jockgrim (DE); Thomas Hankiewicz, Karlsruhe (DE); Frank Probst, Herxheim bei Landau/Pfalz (DE)

(73) Assignee: Siemens Aktiengesellschaft, Munich (DE)

( * ) Notice: Subject to any disclaimer, the term of this patent is extended or adjusted under 35 U.S.C. 154(b) by 344 days.

(21) Appl. No.: 14/134,518

(22) Filed: Dec. 19, 2013

(65) Prior Publication Data
US 2014/0185035 A1 Jul. 3, 2014

(30) Foreign Application Priority Data
Dec. 20, 2012 (DE) .......................... 10 2012 223 874

(51) Int. Cl.
| | | |
|---|---|---|
| *G01J 3/433* | (2006.01) | |
| *G01J 3/42* | (2006.01) | |
| *G01N 21/39* | (2006.01) | |
| *G01N 21/47* | (2006.01) | |

(52) U.S. Cl.
CPC ................ *G01J 3/4338* (2013.01); *G01J 3/42* (2013.01); *G01J 3/433* (2013.01); *G01N 21/39* (2013.01); *G01N 21/47* (2013.01)

(58) Field of Classification Search
CPC .... G01N 21/31; G01N 21/78; G01N 21/783; G01N 21/274; G01N 2021/0321; G01N 2021/0325
See application file for complete search history.

(56) References Cited

U.S. PATENT DOCUMENTS

| | | | | |
|---|---|---|---|---|
| 5,498,875 | A * | 3/1996 | Obremski | G01J 3/4338 250/458.1 |
| 6,356,350 | B1 * | 3/2002 | Silver | G01N 21/3504 250/343 |
| 7,334,482 | B2 * | 2/2008 | Lehmann | G01L 11/02 73/705 |
| 7,616,316 | B1 | 11/2009 | Silver et al. | |
| 7,710,568 | B1 | 5/2010 | Paige et al. | |
| 8,928,879 | B2 * | 1/2015 | Youngner | G01J 3/457 356/310 |
| 2006/0007429 | A1 * | 1/2006 | Emer | G01J 9/00 356/124 |
| 2008/0080663 | A1 * | 4/2008 | Haerer | G06T 5/002 378/7 |
| 2011/0032516 | A1 * | 2/2011 | Zhou | G01N 21/39 356/73 |
| 2011/0150035 | A1 * | 6/2011 | Hanson | G01K 11/12 374/161 |
| 2011/0302992 | A1 | 12/2011 | Robbins et al. | |

FOREIGN PATENT DOCUMENTS

DE 10238356 A1 * 1/2004 ................ G01J 3/42

* cited by examiner

*Primary Examiner* — Kara E Geisel
*Assistant Examiner* — Dominic J. Bologna
(74) *Attorney, Agent, or Firm* — Cozen O'Connor

(57) ABSTRACT

A method in which the wavelength of the light of a tunable light source is varied periodically over an absorption line of interest for the gas component to measure the concentration of a gas component in a measurement gas based on one of two measurement methods of direct absorption spectroscopy and wavelength modulation spectroscopy and, where in the case of wavelength modulation spectroscopy, the wavelength of the light is additionally sinusoidally modulated at a high frequency and with a small amplitude, where the intensity of the light is detected after transradiation of the measurement gas and processed to yield a measurement result, and where in order to increase the accuracy and reliability of the measurement, the two measurement methods are applied simultaneously during each period, or alternately in consecutive periods, and their results are combined by averaging to form the measurement result.

8 Claims, 3 Drawing Sheets

METHOD FOR MEASURING CONCENTRATION OF A GAS COMPONENT IN A MEASUREMENT GAS

BACKGROUND OF THE INVENTION

1. Field of the Invention

The invention relates to a method for measuring concentration of a gas component based on two measurement methods of direct absorption spectroscopy and wavelength modulation spectroscopy, where the wavelength of the light of a tunable light source is varied periodically over an absorption line of interest for the gas component and, in the case of wavelength modulation spectroscopy, the wavelength of the light is additionally sinusoidally modulated at a high frequency and with a small amplitude, and the intensity of the light is detected after transradiation of the measurement gas and processed to yield a measurement result.

2. Description of the Related Art

DE 102 38 356 A1 discloses a method in which two measurement methods are applied alternately in consecutive periods.

Laser spectrometers are used, in particular, for optical gas analysis in process measurement technology. In this case, a laser diode generates light in the infrared region that is guided through the process gas (measurement gas) to be measured and subsequently detected. The wavelength of the light is tuned to a specific absorption line of the gas component respectively to be measured, the laser diode periodically scanning the absorption line as a function of wavelength. For this purpose, the laser diode is driven periodically by a ramp-shaped or triangular current signal. During the direct absorption spectroscopy (DAS), the concentration of the gas component of interest is determined directly from the reduction in light intensity (absorption) detected at the position of the absorption line. In the case of the wavelength modulation spectroscopy (WMS), during the comparatively slow wavelength-dependent scanning of the absorption line, the wavelength of the generated light is additionally sinusoidally modulated at a high frequency and with small amplitude. The profile of the absorption line is not linear. As a result, harmonics of higher order are also generated in the detector signal or measurement signal. The measurement signal is usually evaluated for a higher harmonic, preferably the second harmonic by phase-sensitive lock-in technique (WMS-If). For small modulation parameters, the detection of the nth harmonic is directly proportional to the nth derivative of the direct measurement signal, and so the designation of derivative absorption spectroscopy is also used for the WMS-If. In the case of the WMS, the evaluation of the measurement signal requires an analytical approximation description of the absorption line.

Wavelength modulation spectroscopy and absorption spectroscopy have specific advantages and disadvantages. WMS is advantageous, in particular, for measuring of low concentrations, because it is better at filtering out noise from the measurement signal. However, in the case of higher concentrations, the approximations required to evaluate the measurement signal become increasingly inaccurate, and so the measuring error rises. The situation is reversed in the case of DAS; because of the higher noise sensitivity, the measuring error is higher for small concentrations. However, since there is no need for an approximation description of the absorption line, the measuring accuracy is better with increasing concentration because the useful signal becomes stronger. It is only at very high concentrations (saturation of the absorption) that the measurement method again becomes more inaccurate.

In a method known from U.S. Pat. No. 7,616,316 B2, there is a switch between various operating modes, in particular between both high and WMS at low concentrations of the gas component to be measured. Thus, it is respectively the measurement method that seems to be most suitable that is applied.

In the case of the method known from the above named DE 102 38 356 A1, the two measurement methods WMS and DAS are applied alternately in consecutive periods, i.e., quasi-simultaneously, and the detected signals are likewise fed alternately to two separate averagings and evaluated in parallel. In the case of WMS evaluation, the results of the DAS evaluation can be used, for example, for calibration. This delivers the freedom from calibration of the direct absorption spectroscopy, and the accuracy of the wavelength modulation spectroscopy.

SUMMARY OF THE INVENTION

It is an object of the invention to increase the accuracy and reliability of a measurement in the case of determining the concentration of a gas component in a measurement gas by using laser spectrometry.

This and other objects and advantages are achieved in accordance with the invention by virtue of the fact that in the case of the method of the type mentioned at the beginning, the two measurement methods, i.e., the direct absorption spectroscopy and the wavelength modulation spectroscopy, are applied simultaneously during each period, or, as already known, alternately in consecutive periods, and that their results are combined by averaging to form the measurement result. The application of two independent measurement methods with combination of their results by averaging renders the measurement as a whole more robust and more reliable. In addition, the measuring accuracy is increased, as explained below.

With $c_A$ being the measured value obtained with the aid of one measurement method (A), such as the direct absorption spectroscopy, and $\Delta c_A$ being the associated measuring error and $c_B$ being the measured value obtained with the aid of the other measurement method (B), such as the wavelength modulation spectroscopy, and $\Delta c_B$ being the associated measuring error, the measurement result $$c = \frac{c_A + c_B}{2}$$

is obtained by forming the arithmetic mean value of the two measured values $c_A$ and $c_B$.

In accordance with the Gaussian error propagation law, it then holds for the error $\Delta c$ of the measurement result c that:

$$\Delta c = \sqrt{\left(\frac{\partial c}{\partial c_A}\right)^2 \cdot \Delta c_A^2 + \left(\frac{\partial c}{\partial c_B}\right)^2 \cdot \Delta c_B^2} = \sqrt{\frac{1}{4} \cdot \Delta c_A^2 + \frac{1}{4} \cdot \Delta c_B^2}.$$

By employing a ratio $\alpha$ of the errors $\Delta c_B$ and $\Delta c_A$ of the individual measurements, i.e., $$\frac{\Delta c_B}{\Delta c_A} = \alpha,$$

the error $\Delta c$ of the measurement result c is yielded as:

$$\Delta c = \sqrt{\frac{1}{4}\Delta c_A^2 + \frac{1}{4}\Delta c_B^2} = \frac{1}{2}\Delta c_A \cdot \sqrt{1+\alpha^2}.$$

Consequently, for $\alpha<\sqrt{3}\approx 1.73$ the accuracy of the measurement result c is greater than the accuracies of the individual measurements.

Owing to the fact that in accordance with one advantageous development of the method according to the invention the results of the two measurement methods are weighted differently in the averaging, it is possible to increase the value range of the ratio $\alpha$, within which the error $\Delta c$ is smaller than the errors $\Delta c_B$ and $\Delta c_A$ of the individual measurements. The measured values $c_A$ and $c_B$ can therefore be averaged with the aid of the ratio of their measuring accuracies:

$$c = \frac{\alpha c_A + \frac{1}{\alpha}c_B}{\alpha + \frac{1}{\alpha}}.$$

The result for the error $\Delta c$ of the measurement result c is then yielded as:

$$\Delta c = \Delta c_A \cdot \frac{\sqrt{\alpha^2 + \frac{1}{\alpha^2}}}{\alpha + \frac{1}{\alpha}},$$

which always signifies an improvement in the measuring accuracy because the quotient is always less than 1. Both with the simple and with the weighted averaging, the greatest improvement in the measuring accuracy is achieved for $\alpha=1$, i.e., when the accuracies of the individual measurements are equal.

As mentioned above, in accordance with the invention the two measurement methods are applied either simultaneously during each period in which the absorption line of interest for the measurement gas is scanned as a function of wavelength, or alternately in consecutive periods. In the last named case, the two measurement methods can be applied alternately in more than two consecutive periods, and their results from the more than two periods can be combined by averaging to yield the measurement result. In the case of three consecutive periods, it follows that one measurement method is applied twice and the other measurement method is applied once. The measuring accuracy can be further increased by applying the respectively more accurate measurement method more often than the more inaccurate method, such as in the ratio of 3:2, 2:1 or 3:1.

When the two measurement methods are applied alternately in consecutive periods, the modulation of the tunable light source can be turned off for direct absorption spectroscopy. Alternatively and in the case of the simultaneous application of both measurement methods during each period, the modulation of the tunable light source can be retained during direct absorption spectroscopy, and the detection signal obtained during the detection of the intensity of the light can be subjected to lowpass filtering to remove the signal components obtained by the modulation for the determination of the direct absorption.

In the simplest case, a single detector is used whose detection signal is evaluated differently depending on the measurement method being applied. Since the detection signals to be evaluated in the direct absorption spectroscopy and the wavelength modulation spectroscopy are of different magnitudes, they must necessarily be differently amplified before they can be digitized and further processed. To this end, it is possible to make use of two different detectors with different downstream signal processing devices. It is also possible to use a single detector downstream of which there are arranged two different signal processing devices and a controllable switchover device lying between them and the detector. The signal processing devices then include different analog amplifiers. In the case of only one detector, it is also possible to provide a single analog amplifier with switchable gain.

When the direct absorption spectroscopy is applied, the absorption maximum of the absorption line and, independently thereof, the half-value width are evaluated so as to determine separate results for the concentration to be measured for the gas component that are combined by averaging to yield the result of the direct absorption spectroscopy which, in turn, is averaged with the aid of the result of the wavelength modulation spectroscopy. The use of the half-value width is particularly suitable for the measurement of very high concentrations of the gas component of interest.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PREFERRED EMBODIMENTS

Figure 1:
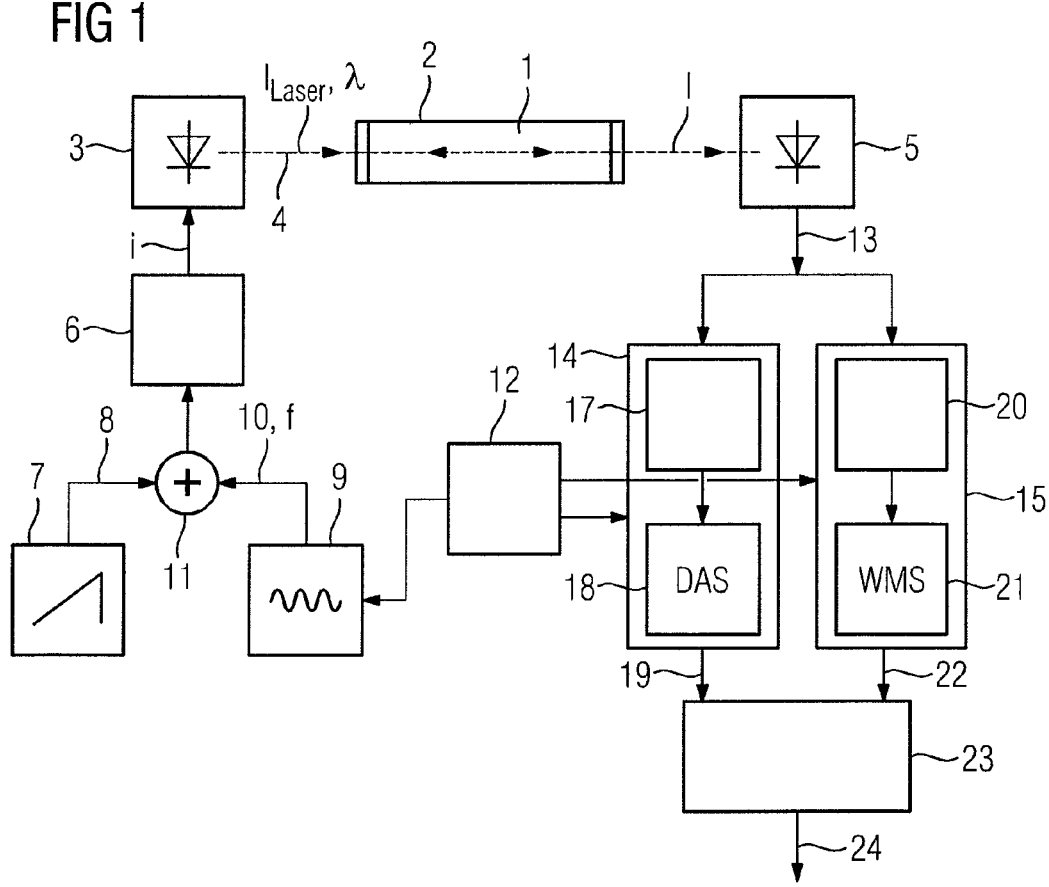
FIG. 1 shows an exemplary embodiment of a laser spectrometer suitable for implementing the method in accordance with the invention.

FIG. 1 is a schematic of a laser spectrometer for measuring the concentration of at least one gas component of interest for a measurement gas 1, which is contained in a measurement volume 2, such as a measurement cell or a process gas line. The spectrometer includes a laser diode 3 whose light 4 falls onto a detector 5 after radiating through the measurement gas 1. The laser diode 3 is driven by a controllable current source 6 with an injection current i, the intensity $I_{Laser}$ and wavelength $\lambda$ of the generated light 4 being a function of the current i and the operating temperature of the laser diode 3. The current source 6 is driven by a first signal generator 7 periodically with the aid of a prescribed current/time function 8, preferably in the shape of a ramp or triangle, in order to scan a selected absorption line of the gas component of interest with the aid of the wavelength λ of the generated light 4, which more or less follows the profile of the current i. A second signal generator 9 generates a sinusoidal signal (modulation signal) 10 of the frequency f, with the aid of which the ramp-shaped current/time function 8 is modulated in a summing element 11. The modulation signal 10 can be switched on and off via a control device 12.

The detector 5 generates, as a function of the detected light intensity I, a detector signal 13 that is evaluated in two different signal processing devices 14, 15, the signal evaluation being performed in the signal processing device 14 after the method of the direct absorption spectroscopy (DAS) and in the signal processing device 15 based on the wavelength modulation spectroscopy (WMS).

Figure 2:
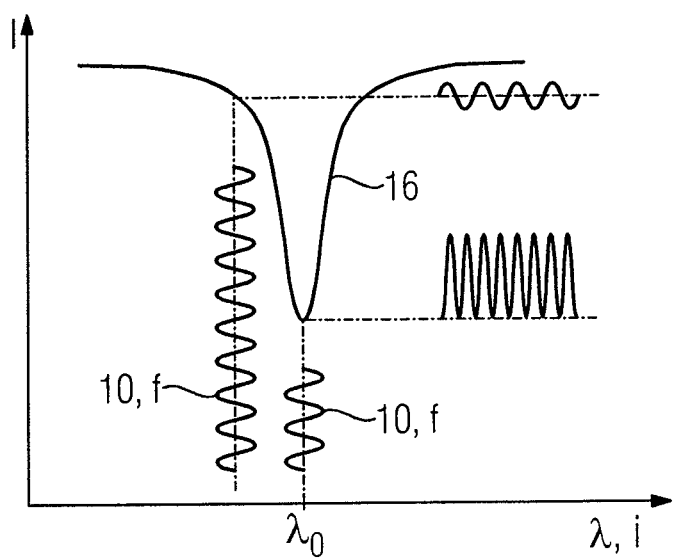
FIG. 2 shows an example of the wavelength-dependent scanning of an absorption line.

By way of example, FIG. 2 shows the wavelength-dependent absorption (reduction in the light intensity I) in the region of a selected absorption line 16 of the gas component to be detected. In the case of the direct absorption spectroscopy, the modulation signal 10 (FIG. 1) is turned off so that absorption is directly detected, and the detector signal 13 corresponds substantially to the absorption line 16. In the case of wavelength modulation spectroscopy, the modulation signal 10 is switched on. Because of the nonlinearity of the absorption line 16, the modulation of the current i of the laser diode 3 with the aid of the frequency f produces a corresponding variation in the light intensity I with more or less strong harmonic distortions, the second harmonic with the frequency 2f dominating at the point of the absorption maximum (middle wavelength $\lambda_0$). In wavelength regions outside the middle of the absorption line 16, by contrast, the component of the second harmonic decreases sharply in the intensity I of the light 4. The absorption that occurs at the point of the absorption maximum can therefore be determined with the aid of an analytical approximation description of the ideal Lorentz-shaped absorption line, and by evaluation of the 2f signal component in the detected light intensity I. It is also possible in principle to use any other harmonic for the evaluation.

The control device 12 shown in FIG. 1 activates the two signal processing devices 14 and 15 alternately in consecutive periods of the current/time function 8, the modulation signal 10 being switched off upon activation of the signal processing device 14, and switched on upon activation of the signal processing device 15.

In the case of the evaluation in the signal processing device 14, the detection signal 13 is filtered, amplified and digitized in a preprocessing device 17 before it is further processed in a downstream digital processing device 18 to yield a result 19 of the direct absorption spectroscopy.

In the case of the evaluation in the other signal processing device 15, the second harmonic, i.e., the 2f signal component of the detection signal 13, is amplified in a preprocessing device 20 in a frequency-selective fashion, and further processed in a downstream processing device 21 in a phase-sensitive fashion (lock-in), and evaluated to yield the result 22 of the wavelength modulation spectroscopy.

In a downstream evaluation device 23, the results 19, 22 of the individual measurements (DAS and WMS) are compared with one another and combined by averaging to yield the measurement result 24. If the results 19, 22 of the individual measurements deviate too much from one another, an error report is produced. In order to raise and/or to check the reliability of the measurement, secondary parameters of the absorption line 16 determined in the evaluation of the individual measurements can be compared with one another. Thus, in the case both of the DAS and of the WMS for the evaluation of the detection signal 13, the line width, the position of the line and the laser power and its variation are determined via a measurement (by varying the current i through the laser diode 3). An error report or warning is thus also produced when in the case of more or less corresponding results 19, 22, for example, the values determined for the line width diverge from one another by more than a prescribed measure.

In order to form the measurement result 24, the individual results 19, 22 can be averaged uniformly or weighted differently, as has already been explained in more detail above, for example. The individual results 19, 22 can be averaged from two or more consecutive periods, the two measurement methods DAS and WMS being applied equally, or differently, often.

In the case of the exemplary embodiment shown in FIG. 1, the control device 12 activates the two signal processing devices 14 and 15 alternately. Alternatively, the detector 5 can be provided with a switchover device that is controlled by the control device 12 and feeds the detection signal 13 alternately to one and the other signal processing device 14, 15.

It is possible to dispense with controlling the second signal generator 9 by the control device 12 for the purpose of turning off the modulation signal 10 during direct absorption spectroscopy. In this case, the detection signal 13 is subjected to lowpass filtering in the preprocessing device 17 of the signal processing device 14 to suppress the frequency components caused by the modulation. It is then possible, for example, also to determine the individual results 19, 22 from DAS simultaneously during each period of the current/time function 8, and to combine them to yield the measurement result 24. The control device 12 is omitted in this case.

Figure 3:
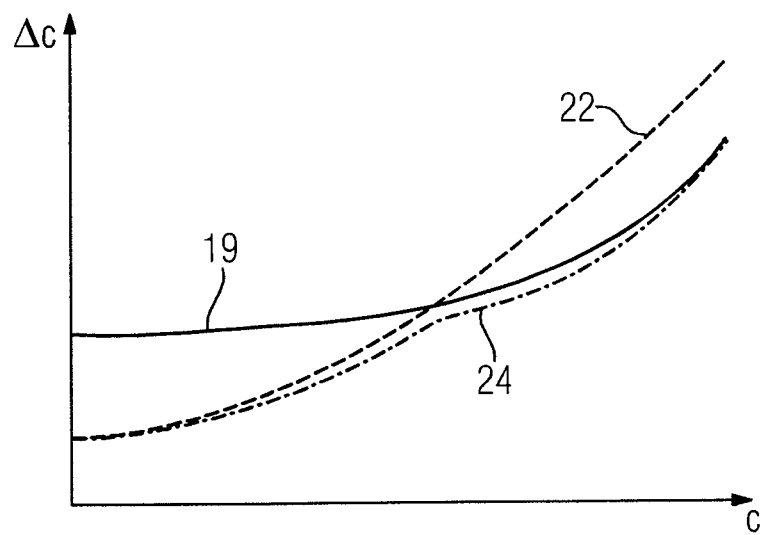
FIG. 3 shows an example of the error dependence of the results of the DAS and WMS individual measurements, and of the measurement result in the case of combination of the individual measurements.

FIG. 3 shows, by way of example, the error dependence of the results of the DAS and WMS individual measurements 19, 22 and of the measurement result 24 formed from then. For the different measurement methods, in the case of the same concentration c of the gas component of interest, the result is different measurement errors Δc. Given small concentrations c, the WMS measurement method 22 is advantageous because noise can be better filtered out from the measurement signal. Given higher concentrations c, however, the approximations required to evaluate the measurement signal become more inaccurate, and so the measuring error Δc rises. By contrast, because of the higher noise sensitivity, the measuring error Δc is higher given small concentrations c in the case of the DAS measurement method 19. Since, on the other hand, there is no need for an approximation description of the absorption line 16 (FIG. 2), the measuring accuracy improves with increasing concentration c because the useful signal becomes stronger. In the case of the DAS measurement method, the absorption maximum or, preferably given very high concentrations c, the half-value width of the absorption line 16 can be evaluated in order to determine the concentration. Here, as well, it can be advantageous to determine the concentration both with the aid of the absorption maximum and based on the half-value width separately, and to combine the two results by averaging.

As mentioned above, the individual results 19, 22 can be averaged from three or more consecutive periods, the two measurement methods DAS and WMS being applied equally, or differently, often. If the concentration c to be measured lies in a region in which the two measurement methods exhibit approximately the same accuracy, the individual results 19, 22 are preferably uniformly averaged. Given concentration values c for which the two measurement methods differ in accuracy, the respectively more accurate measurement method is prioritized in the averaging; this is the WMS in the case of low c, and the DAS in the case of high concentrations.

The inventive method is suitable for spectrometers in all bandwidths (UV, VIS, IR).

Figure 4:
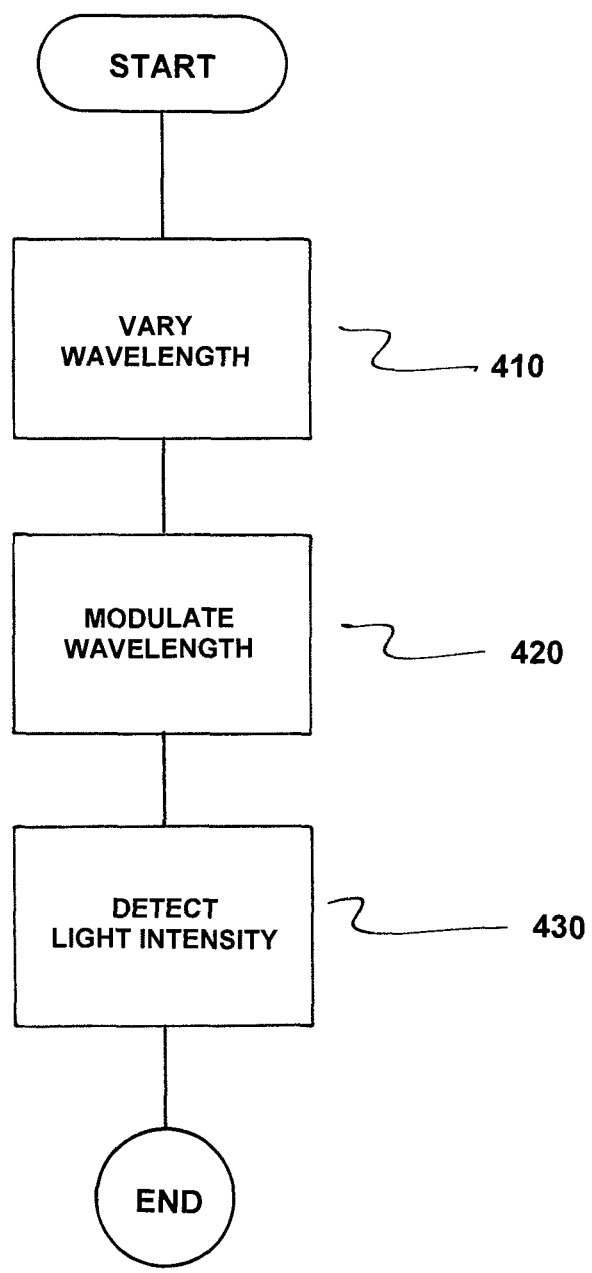
FIG. 4 is a flowchart of the method in accordance with the invention.

FIG. 4 is a flowchart of a method for measuring the concentration of a gas component in a measurement gas based on two measurement methods comprising direct absorption spectroscopy and wavelength modulation spectroscopy. The method comprises varying the wavelength of light of a tunable light source periodically over an absorption line of interest for the gas component, as indicated in step 410.

Next, the wavelength of the light of the tunable light source is additionally sinusoidally modulated at a high frequency and with a small amplitude in cases of wavelength modulation spectroscopy, as indicated in step 420.

The intensity of the light after transradiation of the measurement gas is then detected and the light is processed to yield a measurement result, as indicated in step 430. Here, the two measurement methods are applied simultaneously during each period, or alternately in consecutive periods, and their results are combined by averaging to form the measurement result.

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for measuring concentration of a gas component in a measurement gas based on two measurement methods comprising direct absorption spectroscopy and wavelength modulation spectroscopy, comprising:

varying a wavelength of light of a tunable light source periodically over an absorption line of interest for the gas component;

additionally sinusoidally modulating a wavelength of the light of the tunable light source at a high frequency and with a small amplitude in cases of wavelength modulation spectroscopy; and detecting an intensity of the light after transradiation of the measurement gas and processing the light to yield a measurement result, the two measurement methods being applied simultaneously during each period, or alternately in consecutive periods, and their results being combined by averaging to form the measurement result;

wherein results of the two measurement methods are weighted differently in the averaging; and wherein the results of the two measurement methods are weighted aided by a ratio of their measuring accuracies.

2. The method as claimed in claim 1, wherein the two measurement methods are applied alternately in a plurality of consecutive periods, and their results from the plurality of consecutive periods are combined by averaging to yield the measurement result.

3. The method as claimed in claim 1, wherein the modulation of the tunable light source is switched off during direct absorption spectroscopy.

4. The method as claimed in claim 1, wherein the modulation of the tunable light source is retained during direct absorption spectroscopy, and a detection signal obtained during detection of the intensity of the light is subjected to lowpass filtering.

5. The method as claimed in claim 1, wherein two different detectors with different downstream signal processing devices are implemented.

6. The method as claimed in claim 1, wherein a single detector is implemented.

7. The method as claimed in claim 6, wherein two different signal processing devices are arranged downstream of the detector and a controllable switchover device is arranged between the two different signal processing devices and the detector.

8. The method as claimed in claim 1, wherein, during direct absorption spectroscopy, an absorption maximum and a half-value width of the absorption line are evaluated so as to determine separate results for the concentration to be measured for the gas component which are combined by averaging to yield the result of the direct absorption spectroscopy.

* * * * *